United States Patent
Klooster et al.

(10) Patent No.: US 6,597,446 B2
(45) Date of Patent: Jul. 22, 2003

(54) HOLOGRAPHIC SCATTEROMETER FOR DETECTION AND ANALYSIS OF WAFER SURFACE DEPOSITS

(75) Inventors: Alex Klooster, Ann Arbor, MI (US); James M. Marks, Saline, MI (US); Takeo Sawatari, Bloomfield Hills, MI (US)

(73) Assignee: Sentec Corporation, Walled Lake, MI (US)

(*) Notice: Subject to any disclaimer, the term of this patent is extended or adjusted under 35 U.S.C. 154(b) by 7 days.

(21) Appl. No.: 09/815,228

(22) Filed: Mar. 22, 2001

(65) Prior Publication Data

US 2002/0159052 A1 Oct. 31, 2002

(51) Int. Cl.[7] ............... G01N 21/00; G01N 21/86
(52) U.S. Cl. ............... 356/237.2; 356/237.3; 356/237.4; 356/237.5; 250/559.4; 250/559.41; 250/559.45
(58) Field of Search ............... 356/237.1, 237.2, 356/237.3, 237.4, 237.5; 250/559.4, 559.41, 559.45

(56) References Cited

U.S. PATENT DOCUMENTS

| | | | |
|---|---|---|---|
| 4,986,659 A | * | 1/1991 | Bachalo ............... 356/336 |
| 5,030,842 A | | 7/1991 | Koshinaka et al. ......... 250/571 |
| 5,241,369 A | | 8/1993 | McNeil et al. ............... 356/445 |
| 5,343,290 A | | 8/1994 | Batchelder et al. ......... 356/349 |
| 5,486,919 A | | 1/1996 | Tsuji et al. ............... 356/349 |
| 5,703,692 A | | 12/1997 | McNeil et al. ............... 356/445 |
| 5,923,423 A | * | 7/1999 | Sawatari et al. ......... 356/237.5 |
| 6,008,887 A | * | 12/1999 | Klein et al. ............... 356/28.5 |
| 6,081,325 A | | 6/2000 | Leslie et al. ............... 356/237.2 |
| 6,137,570 A | * | 10/2000 | Chuang et al. .......... 356/237.5 |
| 6,255,666 B1 | * | 7/2001 | Brunfeld et al. ....... 250/559.45 |
| 6,400,454 B1 | * | 6/2002 | Noguchi et al. ......... 356/237.3 |
| 6,411,377 B1 | * | 6/2002 | Noguchi et al. ......... 356/237.4 |
| 2002/0044278 A1 | * | 4/2002 | Le ........................... 356/237.3 |
| 2002/0171825 A1 | * | 11/2002 | Krantz et al. ............. 356/237.1 |
| 2002/0180985 A1 | * | 12/2002 | Wack et al. ............... 356/600 |
| 2002/0191179 A1 | * | 12/2002 | Tukker et al. ........... 356/237.2 |
| 2003/0011760 A1 | * | 1/2003 | Vaez-Iravani et al. ... 356/237.2 |
| 2003/0011786 A1 | * | 1/2003 | Levy et al. ................. 356/660 |

* cited by examiner

Primary Examiner—Evelyn Lester
(74) Attorney, Agent, or Firm—Kevin G. Mierzwa

(57) ABSTRACT

A holographic scatterometer with continuous readout can rapidly identify the presence of deposits (particles or other defects) on an unpatterned wafer surface and determine the volume density (size) and location. The scatterometer can also determine chemical composition of the detected deposits. The range of the deposit (particle) size to be measured is below 80 nm, which currently existing scatterometer type instruments cannot readily detect. The inspection can be achieved as an in-line stage during the processing of wafers or in situ in combination with another processing tool or as a separate off-line analysis device.

29 Claims, 5 Drawing Sheets

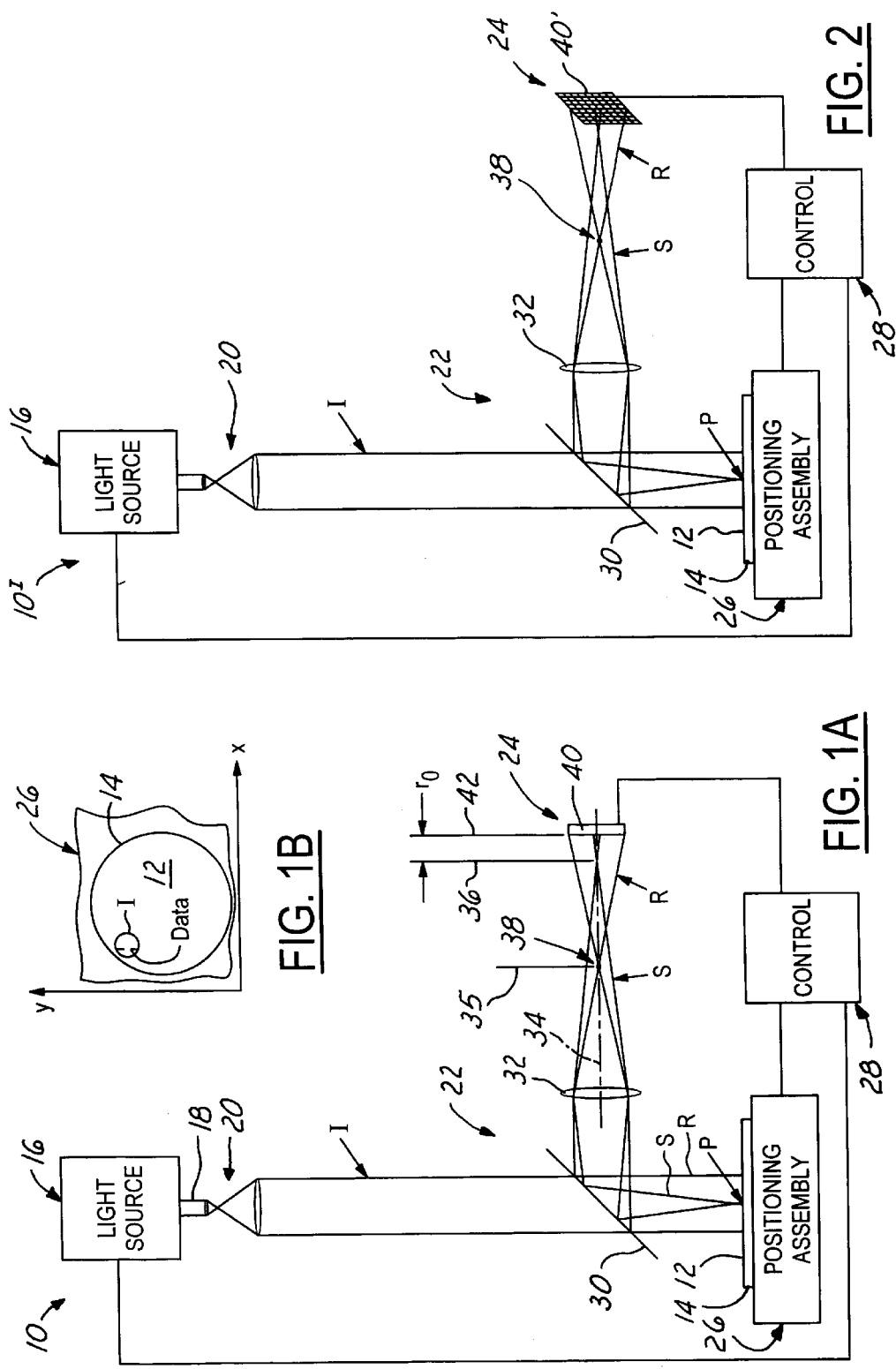

HOLOGRAPHIC SCATTEROMETER FOR DETECTION AND ANALYSIS OF WAFER SURFACE DEPOSITS

STATEMENT AS TO RIGHTS TO INVENTIONS MADE UNDER FEDERALLY SPONSORED RESEARCH AND DEVELOPMENT

A portion of the work described herein was supported by United States Air Force (ASAF)/AFMC/ASC under contract no. F33615-96-C-5108. The government may have certain rights.

BACKGROUND OF THE INVENTION

1. Technical Field

This invention relates generally to optical inspection instruments and, more specifically, to such instruments that inspect a surface of interest, such as a wafer, for example during in-line processing.

2. Discussion of the Related Art

There has been much investigation in the field of inspection systems. In particular, inspection systems are needed in the semiconductor industry for inspecting wafers. The significance for detecting and identifying submicron surface defects on such wafers is due in part to the present semiconductor industry move from 0.250 micron to 0.180 micron and, in less than ten years, to 0.130 micron fabrication architectures. The latter architecture is so exacting that it will require the detection of 2 nm substrate defects and 40 nm sized particles on unpatterned silicon wafers. In addition, the industry is scaling up from 200 mm to 300 mm diameter wafers with fewer defects commercially permitted, and rapid detection required at all processing stages. The current industry projection is that about 9% of all wafer production will use the 300 mm format by the year 2002. To meet these needs, defect data must be processed in near-real-time to allow correction of processing problems through, for example, statistical process control (SPC) techniques.

Many surface roughness inspection systems are available. These include: high resolution microscopes such as the atomic force microscope, optical microscopes such as the phase contrast microscope, other optical measurement systems such as ellipsometers, and mechanical contact methods that use a stylus. For sub-micron resolution, most of these techniques are not suitable for in-process surface inspection. High-resolution microscopes require cumbersome surface preparations and expensive operations. Optical microscopes, in general, do not have sufficient resolution and accuracy. Ellipsometry or spectroscopy also do not provide adequate surface roughness information. Mechanical stylus devices are simply out of the question.

Among the possible methods is the optical heterodyne (frequency-shifted) microscope. The heterodyne microscope is an interferometric microscope where the signal beam is frequency-shifted relative to a reference beam. With this method, the signal containing the optical phase information (surface roughness) can be electronically detected by comparing the phase of the beams from different portions of the wafer surface. The problems with this method are: (a) a critical focusing requirement, (b) low throughput rate due to slow scanning, (c) inadequate lateral resolution (>0.2 mm), (d) limited sensitivity (<100 nm), and (e) inadequate information on the surface deposit materials. In particular with regard to problem (b), a serious drawback with microscopy, in general, is in assessing the number of defects over a large wafer area by scanning with a micron-sized area of view. This would require hours, if not days, to view an entire wafer surface even with a multiple array of detectors.

Another candidate technology, namely scatterometry, has a drawback as presently, generally implemented. A significant limitation with scatterometry is that the intensity of scattering is typically measured at oblique angles, excluding the specular beam. Under this condition, the diameter of particles that can be realistically detected using an in-line tool must be greater than 80 nm (i.e., in order to capture enough light to detect particles, the particle size must be greater than about 80 nm.

U.S. Pat. No. 5,343,290 to Batchelder, et al describes a dark field illumination heterodyne interferometer for particle detection. A heterodyne interferometer is combined with a dark field illumination for improved surface particle detection sensitivity. The U.S. Pat. No. 5,486,919 to Tsuji also describes an optical heterodyne interferometer to detect defects on patterned wafers utilizing different states of polarization for incident and scattered light. The Batchelder and Tsuji heterodyne interferometers provide photon counting detection (Shot noise limited) for the small scattered light from the particles, although the grazing illumination described in both patents will only provide lower sensitivity (only good for a larger particle detection). The problem with these methods is that they cannot effectively discriminate particles on the wafer surface, (which are desired to be detected) from particles within the beam suspended in the air, (which are not desired to be detected.)

U.S. Pat. No. 5,030,842 to Koshinaka, et al describes a method to detect particles using two illumination beams, where the phase of one beam with respect to the other is modulated so that the detected light scattered from a particle in the illuminated area can be distinguished from all other light. As they point out in their patent, however, it will detect particles suspended in the air as long as they are within the overlapped region of the two illumination beams. This will increase a chance of producing a false signal.

U.S. Pat. No. 6,081,325 to Leslie, et al describes a sophisticated scatterometer, which can detect defects and particles on unpatterned and patterned wafer surfaces. The system uses several photo-multiplier tubes and a charge-coupled detector (CCD) camera. A focused laser beam illuminates the sample surface and the light scattered from a particle or defect is monitored by these multiple numbers (4) of photo-multiplier tubes. Utilizing the asymmetrical nature of scattering from particles or defects, the system discriminates between defects (or particles) and the wafer pattern. In addition they use a CCD camera and obtain an image of the sample surface illuminated by the focused laser beam: light scattered from only the illuminated spot is focused on a pixel of CCD camera. The wafer is scanned multiple times to provide a desirable image. However, this imaging method does not provide photon-counting detection. Also, the rescanning of the surface is time consuming a particularly undesirable for commercial applications.

The objective of the present invention is to overcome these shortcomings of the existing devices and to achieve photon detection using a CCD camera, and to completely discriminate between particles on a sample surface and those suspended in air. This is achieved without using any external frequency shift or phase modulation device and focused illumination beam scanning.

SUMMARY OF THE INVENTION

In accordance with the present invention, an apparatus is provided for inspecting a surface of an object. The apparatus includes the following major parts: a light source, a photodetector, an optical assembly, a positioning assembly, and a controller. The light source is configured to generate an illumination light beam. The illumination beam, when incident upon a particle on the surface, is scattered to define a scattered beam. The optical assembly is configured to direct the scattered beam and a reference beam, derived from the illumination beam, to the photodetector. The positioning assembly is configured to move the object such that the surface moves relative to the illumination beam. Finally, the controller is coupled to the photodetector and is configured to detect the presence of the particle in accordance with an interference pattern from a superposition of the reference beam and the scattered beam.

The invention is suitably adapted for use in the inspection of semiconductor wafers, using optical detection to holographically record light scattered from a particle on a wafer surface illuminated with, in a preferred embodiment, a laser or other coherent source. The invention utilizes two beams, at least one of which is incident on a wafer surface. These two beams are preferably derived from the same source and are subsequently re-combined to form the above-mentioned interferometric pattern. In one embodiment, a geometrical configuration is used such that the illumination beam strikes the surface at normal or near normal incidence. A specular reflection of the illumination beam from the wafer surface is used as the reference beam and is interferometrically combined with light backscattered (the "scattered beam") from any contaminant particles on the surface. The device, when used in a preferred environment, is especially effective for scanning unpatterned semiconductor wafers, since they have only a relatively few, isolated contaminant particles present.

In a preferred embodiment, the light source may comprise conventional apparatus, such as a diode-pumped solid-state laser, a multiple wavelength ion laser, or even a partially coherent source like a "white-light" Xenon lamp. In operation, a wafer surface is illuminated by the illumination beam. The scattered light from a deposit (particle) is detected as a fringe pattern formed by the interference between the scattered light and a reference beam generated from the same light source. The interference pattern will be a spatially fluctuating component of the light power, which can be detected using the photodetector.

In another preferred embodiment, the interference pattern is preserved during scanning. This is accomplished by using Time Delay and Integration (TDI). In particular, the preservation is accomplished by transporting the wafer surface such that the modulated light signal (i.e., interference pattern) moves across the face of the photodetector in synchronism with an electronic position shift of the register portions of the photodetector. Since the shifting of the image data in the registers is substantially locked to the scanning speed of the wafer, the inspection apparatus according to the invention is basically immune against background optical noise, such as that caused by scattering particles in the air. In the described embodiment, the apparatus may operate as a "photon-counter", limited only by the quantum effect shot noise.

In yet another embodiment, composition analysis of detected particles is performed. The composition analysis of such a contaminant particle is carried out using a spectrometer. By analyzing the spectrum of the interference pattern using predetermined data, the composition of the contaminant can be identified.

Inasmuch as the amplitude of the scattered signal is proportional to the volume of the contaminant particle, the controller can determine volume density. The apparatus detects the scattered beam as a modulation pattern caused by the interference between the reference beam and the scattered beam. This interference pattern can be detected with, in a preferred embodiment, a CCD camera.

In such embodiments employing a CCD camera, the CCD camera may be configured in a variety of ways including, but not limited to, both a linear scanning array and an area array. This latter configuration can function as an integrating device or as a frame transfer camera. As an integrating device, the CCD camera may be controlled by the controller to operate as a TDI sensor. In this technique, the detector array registers are clocked so that the charge packets are transferred in a manner synchronous to the movement of the wafer by the positioning assembly. Image data analysis may be conducted using conventional digital signal processing methods.

With this interferometric detection apparatus, weak scattering from particles in the range of 20 nm to 100 nm in size may be detected. This compares to conventional scatterometry which can, at best, detect 80 nm or larger particles. The amplitude of the scattered light is also dependent on the refractive index of the particle. Since, in one embodiment, the apparatus can provide spectroscopic data (which varies in response to different wavelengths) of the deposit (particle), it can be used to identify the composition of surface contaminants. Finally, since the surface to be inspected moves in accordance with a predefined motion relative to the scanning beam, erroneous detection of particles suspended in the air may be avoided.

One advantage of the invention is that high resolution may be obtained. In prior systems if two particles fell within one pixel no discrimination could be obtained. The present invention allows this situation to be distinguished and categorized by size and location.

These and other objects of this invention will become apparent to one skilled in the art from the detailed description and the accompanying drawings illustrating features of this invention by way of example.

BRIEF DESCRIPTION OF THE DRAWINGS

FIG. 1A is a diagrammatic representation of a linear array holographic scatterometer embodiment according to the present invention.

FIG. 1B is an exaggerated, top view of a surface to be inspected.

FIG. 2 is a diagrammatic representation of an area array holographic scatterometer embodiment according to the present invention.

DETAILED DESCRIPTION OF THE PREFERRED EMBODIMENTS

Figure 4:
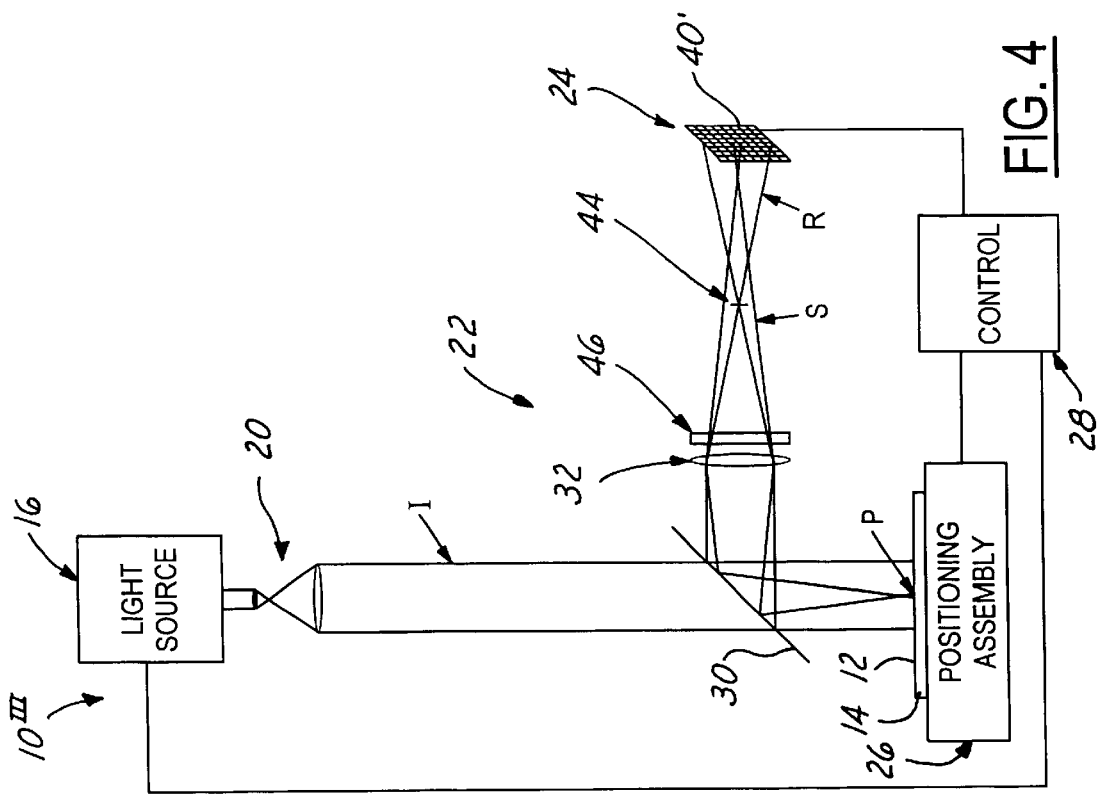
FIG. 4 is a diagrammatic representation of a multichannel holographic scatterometer embodiment according to the present invention.

Referring now to the drawings wherein like reference numerals are used to identify identical components in the various views, FIG. 1 shows an apparatus 10 for inspecting a surface 12 of an object, such as a semiconductor wafer 14 (preferably, unpatterned). Although the preferred embodiments will be described in connection with the inspection of an unpatterned semiconductor wafer, it should be understood that the present invention is not so limited, and may be applied to other environments where detecting (and alternately determining the composition of) particles on an otherwise contaminant particle free surface is desirable or required.

Before proceeding to a detailed description, a general overview of the invention will be set forth. Small particles on an unpatterned wafer surface are often undesirable and must be detected for remedial action. As will be described in detail hereinafter, embodiments of the present invention are configured to establish an interference fringe pattern when such particles are present. In two dimensions, the fringe pattern is similar to a series of concentric rings varying through a complete range of intensities from substantial destructive interference (dark) to substantial constructive interference (light). A section through the rings appears similar to a sinusoid. Such a pattern may be detected in a fairly straightforward manner if the fringe rings are "compressed". As used in this specification, "compress" or "compression" means transforming a dispersed interference signal (i.e., from a particle) and collapsing or compressing it to a specific spatial location relative to a wafer surface. This compression may be done in either one or two orthogonal dimensions either optically or digitally (Note: the fringe pattern is a spatial two dimensional phenomena as opposed to frequency which is a temporal or time dependent determination). Once "compressed", the detection of the interference pattern is representative of the presence of a foreign particle on the wafer surface. Finally, since foreign particles in the air do not move in synchronism with the wafer surface/CCD image movement, any interference is effectively "smeared" out.

Referring now to FIG. 1, apparatus 10 includes a light source 16 configured to generate a source light beam 18 and which further includes an expanding and collimating assembly 20, an optical assembly 22, a photodetector 24, a positioning assembly 26, and a controller 28.

Light source 16 may comprise conventional apparatus known to those of ordinary skill in the art, including, but not limited to, Argon lasers (multiple lines), diode-pumped solid-state lasers, quasi-coherent sources such as Xenon arc lamps, and the like. For exemplary purposes only, an embodiment of the disclosed invention may comprise a diode-pumped solid-state (DPSS) laser having low noise, such as that commercially available, referred to as a "Verdi" laser, manufactured by Coherent, Inc., having an output greater than 5.0 Watts, continuous, for example at a single frequency such as 532 nanometers. In an alternate embodiment, a multi-line light source may be used, such as that commercially available and referred to as a "BeamLok 2080", available from Spectra Physics. Such a multi-line light source may be a water-cooled ion-laser, configured for 25 watt, multi-line Argon or 5 watt multi-line Krypton operation (and featuring active beam stabilization). Regarding wavelength selection, it should be understood that, due to particle scattering effects, relatively shorter wavelengths are preferable; however, this factor must be balanced against the available illumination sources of sufficient intensity. The fringe pattern does not change, substantially, for multiple wavelengths (i.e., at least taken one at a time) or even for partially coherent sources (although the modulation of the fringe pattern may be reduced).

Light source 16 further includes expanding and collimating assembly 20, which is configured to produce an illumination beam, designated "I" in the drawings, from source light beam 18, and for directing illumination beam I toward, or in other words, in the direction of, surface 12. Assembly 20 may include a condenser lens, and a collimator, each of which may be conventional apparatus known to those of ordinary skill in the art. Illumination beam I, when incident upon a particle on the surface 12 of object 14, creates a cone of backscattered light defining a scattered beam, designated "S" in the drawings. Illumination beam I is also specularly reflected by surface 12 to define a reference beam, designated in the drawings as "R."

Optical assembly 22 is configured to generally direct the scattered light beam S and the reference light beam R to photodetector 24. Optical assembly 22, in the embodiment illustrated in FIG. 1A, includes a beam-splitter 30, focusing optics such as a spherical lens 32 having an optical axis 34, a focal point 35 and a focused image plane 36 respectively associated therewith, and a neutral density filter 38. Beamsplitter 30, lens 32, and neutral density filter 38 may comprise conventional apparatus known to those of ordinary skill in the art.

Photodetector 24 is provided for detecting an intensity (or light power) of the light impinging thereon, and converting the same into a light intensity signal, which may be a voltage signal whose amplitude corresponds to light power. Photodetector 24 may comprise conventional apparatus wellknown to those of ordinary skill in the art. In the embodiment illustrated in FIG. 1A, photodetector 24 comprises a camera having a linear array charge-coupled device (CCD) 40, which has a detection plane 42 associated therewith. For purposes of example only, linear array CCD 40 may comprise commercially available components such as model no. CL-CB-2048T, available from Dalsa, having 2048 pixels wherein the intensity of each pixel is capable of being converted to a 12-bit digital word, and further having a data rate of 20 megahertz. Such device has a relatively good dynamic range, anti-blooming exposure control, and multicamera synchronization.

Positioning assembly 26 is configured to move wafer 14 such that surface 12 moves relative to the illumination beam I in accordance with a drive control signal generated, for example, by controller 28.

FIG. 1B illustrates the orientation of the movement established by positioning assembly 26 under the control of controller 28. FIG. 1B shows wafer 14, including surface 12, disposed proximate positioning assembly 26 (shown in diagrammatic, fragmentary fashion). For purposes of the present description, "scanning" occurs in a direction parallel to the x-axis. FIG. 1B also shows illumination beam I, in exaggerated form. In the illustrated embodiment, the illumination beam remains fixed in absolute space, while positioning assembly 26 moves wafer 14. Thus, for purposes of example only, assume that it is desired to inspect the wafer surface 12 in an increasingly positive x-axis direction (i.e., from left-to-right relative to the orientation in FIG. 1B), then positioning assembly 26 would move the wafer 14 in the negative x-axis direction (i.e., from right-to-left). Of course, due to optical assembly 22 (and the inverting nature of a spherical lens), the image of surface 12 moves in a negative x-axis direction across photodetector 24. Expanding and collimating assembly 20, and optical assembly 22 are, in one embodiment, operative to direct to surface 12 an illumination beam I having an approximately diameter of 35 millimeters, and having an effective usable area in a center region thereof approximately 20 millimeters on each side (i.e., a square region). Moreover, in such an embodiment, the optics are such that the effective pixel size (or sample area) at the wafer surface is approximately 5.0 microns. Apparatus 10, which employs a linear array CCD 40, images (and captures the corresponding light intensity of) a "line" parallel to the y-axis, shown in diagrammatic form in FIG. 1B as a dashed-line designated "data."

After each scanning motion, which is preferably substantially continuous in the x-axis direction, has been completed, positioning assembly 26 is controlled by controller 28 to move or index the wafer 14 for the next scan (i.e., based on the orientation in FIG. 1B, the indexing movement occurs in the y-axis direction). After the entire surface 12 has been inspected, and, provided that apparatus 10 is being used as an "in-line" component in a fabrication process, positioning assembly 26 is further controlled to move wafer 14 to the next processing station. Likewise, positioning assembly, in such an "in-line" configuration, retrieves the next wafer 14 to be inspected.

Positioning assembly 26 thus includes three distinct functions when integrated into an "in-line" fabrication assembly line, namely: (i) handling wafers to and from the inspection position; (ii) substantially continuously moving the wafer in a scanning direction (i.e., x-axis movement relative to the orientation of FIG. 1B); and (iii) indexing movement for subsequent scans (i.e., y-axis movement based on the orientation shown in FIG. 1B) Positioning assembly 26 may comprise conventional apparatus known in the art for carrying out the above-described functions. For example, in one embodiment, wafer handling/positioning may be accomplished by a three-link arm "Gencobot IV" robot, commercially available from Genmark, and which has a 24 inch reach, and is capable of handling, in presently commercially available versions, wafer sizes from 50 millimeters to 300 millimeters. Such a robot may be used in combination with a standalone wafer positioner, such as also available from Genmark. Positioning assembly 26 may further include, with respect to the continuous scan movement, a linear slide positioner such as an "ATS 8000 air bearing stage" commercially available from Aerotech, which is a highly accurate, repeatable, high-speed drive system with up to 600 millimeter of travel range, and is designed for wafer stepping and transport. It bears repeating that this device provides motion in the continuous-scan direction of apparatus 10. Positioning assembly 26 may further include an indexer which may include commercially available components such as a model "106008ET stage" from Parker Daedal, and a model "Zeta 57-51" microstepper system from Compumotor. The indexer is adapted for inspection applications and will index, as described above, wafer 14 to subsequent scanning positions.

Controller 28 is coupled to light source 16, photodetector 24, and positioning assembly 26 and is configured to detect the presence of a particle P, if any, in accordance with an interference pattern from a superposition of the reference beam R and the scattered beam S. Controller 28 may comprise a general purpose computer commercially available, having known features such as input/output (I/O), memory (both RAM, ROM), hard drive, and the like. Such a general purpose computer preferably has sufficient computing capabilities to receive data from the scanning of surface 12 via CCD 40, and calculate, in real-time, the presence (i.e., x, y location) and/or composition of foreign particles P on wafer surface 12. In one embodiment, the computer may be a PCI bus based system, employing a 500 megahertz or higher Digital Alpha processor, and having system memory (physical) of at least 256 megabytes. The operating system software may comprise conventional system software such as Microsoft Windows NT or Digital Unix. Conventionally, linear array CCD 40 provides, as an output, an analog representation of the intensities on a per-pixel basis. Accordingly, to facilitate processing in a digital computer, the intensity must be converted into digital format. Accordingly, controller 28 may further include an analog-to-digital converter (not shown) coupled to photodetector 24, which may comprise conventional apparatus. For example, in one embodiment, the A/D converter may be a commercially available model referred to as "MATROX MAGIC" commercially available from Matrox, which is an image processor/frame grabber designed to interface between the above-referred to CCD array and the system control/processing computer 28.

In operation, light from the source is expanded and collimated by optical assembly 20 disposed in front of the source 16. The collimated beam I illuminates wafer surface 12 after passing through beam-splitter 30. Cylindrical optics (not shown in this embodiment) may be added to the optical system to increase the intensity of the illumination beam I at wafer surface 12 for increased efficiency. The reference beam R is specularly reflected by wafer surface 12, reflects from beam-splitter 30 and reaches linear array chip 40, after passing through focusing optics 32. The frequency of this beam is not Doppler shifted, even though it is reflected by the moving wafer surface. The reason for this "no Doppler effect" can be understood from the fact that the distance between the source and the linear array of the CCD camera is unchanged as long as any undulation of wafer surface 12 is a small fraction of the wavelength of visible light.

Simultaneously, if any contaminant particles are present on the illuminated surface of the wafer, a small portion of the light will be backscattered in a spherical radiation pattern, scattered beam S. The light, which is backscattered by any particle P illuminated by the beam I, also propagates to CCD 40 along the same path followed by the reference beam R. Since, in this description, both the reference beam R and the signal or scattered beam S will experience identical phase shifts due to any wafer surface motion, a phase shift problem does not exist.

Both beams (the reference beam R and the backscattered beam S) arrive at CCD detector 40. The detector 40 measures the light power of the two coherently superimposed beams. The total light power comprises a large bias (DC) component and a small spatial interference component. The interference component is a pattern formed by the interference between the two beams. Equation 1 shows the form of the signal detected by a single pixel (located at any arbitrary point, y, and at the scanning measurement time, t) of CCD 40 corresponding to a given wavelength, $\lambda$.

$$I = |a + b(\lambda, t)\exp(ik[(x_0 - vt)^2 + (y_0 - y)^2]/2r_0 + i\theta + i\Delta\theta(t))|^2 \quad (1)$$

$$= |a|^2 + 2|a||b(\lambda, t)|\cos(k[(x_0 - vt)^2 + (y_0 - y)^2]/2r_0 + \theta + \Delta\theta(t))$$

where a is the amplitude of the reference beam (R), and the b ($\lambda$, $\tau$) is the amplitude of the scattered beam which is also modified by the intensity distribution of the illumination beam (I) on the wafer surface. ($x_0$, $y_0$) is the coordinate of the location of the particle in the two-dimensional image plane at time t=0. Note that the coordinate is chosen such that the scanning direction is parallel with the x-axis and the data along a single line (along the y axis) in the image plane are read in at one time. $r_0$ is the "defocus distance", a distance between the focused image plane 36 and the CCD detector plane 42, measured along the optical axis 34 (best shown in FIG. 1A). The scanning velocity of the particle (or the wafer surface) is v. $\theta$ is a constant phase term and $\Delta\theta(t)$ is a phase term due to any jitter which may be introduced by out-of-phase motion of the wafer as explained below. Note that apparatus 10, as implemented, includes a linear array CCD 40, and that the wafer surface is being moved at a substantially constant velocity. Thus, an "exposure" or "dwell" time must be selected (in which the pixels acquire light) so that the data is adequately sampled. It bears emphasizing that the intensity stored by a particular pixel is an accumulation over a relatively small displacement of the wafer surface. Those of ordinary skill in the art have the requisite knowledge to select an appropriate exposure time.

In a conventional scatterometer, one must detect the light power signal of the form $|b(\lambda, \tau)|^2$ which becomes smaller than a noise floor associated with photodetector 40 if the particle size is much less than 80 nm. Using interferometric imaging, the cross-product term, $2|a||b(\lambda, \tau)|$, can be amplified to a level much greater than $|b(\lambda, \tau)|^2$ by selecting an appropriate value of $|a|$. Since this interferometric or cross-product "gain" can be almost arbitrarily large, apparatus 10, operates as a photon counting device limited only by shot noise. The unmodulated or bias component and noise are attenuated by a small attenuator, such as neutral density filter 38, placed at the focal point 35 of the lens system 32. The remainder of the bias component may be removed during the signal processing.

Lens 32 is carefully positioned so that wafer surface 12 is focused at a plane near (i.e., plane 36), but not coinciding with, the CCD camera detector chip (i.e., plane 42). Thus, any interference pattern due to a scattering particle on the wafer will be displayed as a two-dimensional interferogram at CCD 40. The size of the pattern is controlled by the separation between the focus plane and the detector surface, namely $r_o$. As wafer 14 is translated by positioning assembly 26 (in a direction normal to the plane of FIG. 1A), the interferogram will progress past the linear CCD array 40, generating electronic charges which can be continuously read out in a "pipeline" manner, digitized and stored in controller 28. The stored image is then digitally processed using standard image compression techniques.

Raw data gathered corresponds to holograms of a spherical wave (Fresnel zone plate) which can be represented by the following equation:

$$I(x,y) = A + B\cos(k[(x-x_0)^2 + (y-y_0)^2]/2r_0 + \theta), \quad (2)$$

where A is a DC component generated by the reference beam and B is the modulated amplitude of the holographic fringe pattern. The term k=$2\pi/\lambda$, and ($x_0$, $y_0$) describes the location of a particle in the image plane (x, y) at CCD 40 (due to the imaging lens), and $\theta$ is a phase term determined by the phase difference between the spherical wave from particle P and a collimated reference wave R. The defocusing distance, $r_0$, (selected for the data acquisition) is measured from the focused image plane. The reference wave R is assumed to have normal incidence at the CCD 40 image plane. This assumption does not alter the processing method if the reference beam R uses oblique illumination. Mathematically, the data processing can be expressed as follows.

The first step involves removing the "bias" component (the background component due to the reference beam) as completely as possible. For example, by evaluating the following:

$$Iac(x,y) = I(x,y) - \langle I(x,y) \rangle, \quad (3)$$

where <A> represents an average value of A.

This remaining component is the holographic component and is termed the "ac" component in the following explanation. (Note that in this usage of "ac", it means the "spatially" fluctuating components and it may not be the generally used term to express such a component.)

The next step involves applying a "matched filter" for an "ideal" spherical wave (complex function) corresponding to the expected spherical wavefront from a particle on wafer surface 12.

In one embodiment, the "matched filter" is implemented by multiplying the expected spherical wavefront by the actual ac component of the captured signal, Iac(x, y), integrating the product over (x, y), and applying this multiplication and integration process over the entire image (by shifting the relative position between the filter function and the image data and repeating the multiplication and integration). To the extent the ac component is comprised of noise, the positive and negative excursions can be expected to be random. Thus, filtering such a random ac component by the expected waveform can be expected to "net out" to approximately zero.

However, if an interference pattern is contained in Iac(x, y), then filtering by the expected waveform will produce a detectable, positive value.

This filtering process can be expressed by:

$$Ipro(u,v) = \langle Iac(x,y) * r((x-u),(y-v)) \rangle, \quad (4)$$

where Ipro(u, v) is the final processed image. The coordinates (u, v) correspond to the image coordinate (x, y) The expected spherical wave r(x, y) is given as:

$$r(x,y) = \exp(ik(x^2+y^2)/2r_0). \quad (5)$$

It is to be noted that the above expression is given by the continuous coordinates (x, y) and by (u, v). If a CCD camera is used, these will correspond to individual pixel element locations (m, n) and (m', n') as follows:

$$(x, y) = (m\Delta a, n\Delta b)$$

and $$(u, v) = (m'\Delta a, n'\Delta b), \quad (6)$$

where $\Delta a$ and $\Delta b$ are the spacings between the CCD's adjacent pixel elements.

The resultant image obtained through this matched filter operation is a point. This matched filtering operation can be implemented in a Fourier transform plan and is well known in the art of performing filtering operations. A Fourier transform may be achieved using an FFT (Fast Fourier Transform) algorithm. This approach may shorten the calculation time when the waveform r(x, y) is complex.

The foregoing "matched filter" operation is sometimes also referred to as a cross-correlation. In addition, for these small particle sizes, the scattering signature is proportional to the particle's volume. A "volume density" may then be determined for the wafer (i.e., the population distribution for contaminant particles "large" enough to be considered "killer" defects.) Note that the basic signal-to-noise of the system is limited by the optical power that one can use. The maximum optical power is determined by the threshold value which might cause damage to the wafer surface.

FIG. 2 illustrates another embodiment, particularly apparatus $10^I$. Apparatus $10^I$ is nearly identical to apparatus 10 except that the linear CCD array 40 in the camera has been replaced by a two-dimensional area CCD array 40' operating in a time delay and integrating (TDI) mode. For example, in one embodiment, CCD 40' may be a commercially available device, such as model no. "CT-E3-4069A" from Dalsa, having 4096 pixels in 96 TDI "stages", and which may have a data rate of 200 MHZ, and a line rate of 44 Khz.

Using the camera 40' in this way, the CCD registers are clocked so that the electronic charge packets are transferred at the same rate and in the same direction as the image. This ensures that the signal charge building up in the CCD remains aligned under the same part of the image (of the wafer surface). In this way, the image signal (of the wafer surface) can be integrated for a much longer time than is allowed by the temporary storage time of a single pixel. The sensitivity of the sensor is increased by a factor roughly equal to the number of "stages" in the scan direction. Hence, this method can be used for very low light levels or, as in the present application, at very high scan speeds. Data is being simultaneously collected and transferred out as the wafer scan is in progress. It has the further advantage of averaging out any non-uniformities in each column and gives an enhanced signal to noise ratio.

In-process wafer inspection assumes a short inspection time. In order to accomplish rapid inspection, a charge coupled device (CCD) array operating in the TDI mode is employed. This allows continuous data collection and readout from the CCD with substantially no "dead time" during readout and wafer translation. It is well known that the noise level of CCDs is greater than that of silicon photo-detectors. However, if one uses the appropriate procedure, a CCD array can be used for detection of particles smaller than 80 nm. By using multiples of such a unit, if necessary, one can easily examine the entire wafer surface in less than one minute as follows. At the specified CCD array line rate of 44 KHz, the continuous scanning speed of the wafer surface could be as large as 220 mm/sec with a nominal speed of 150 mm/sec. This would allow the complete scanning of a 300 mm diameter wafer in less than a minute, including the loading and retrieval times.

Signal processing is the same as described above in connection with apparatus 10.

Figure 3:
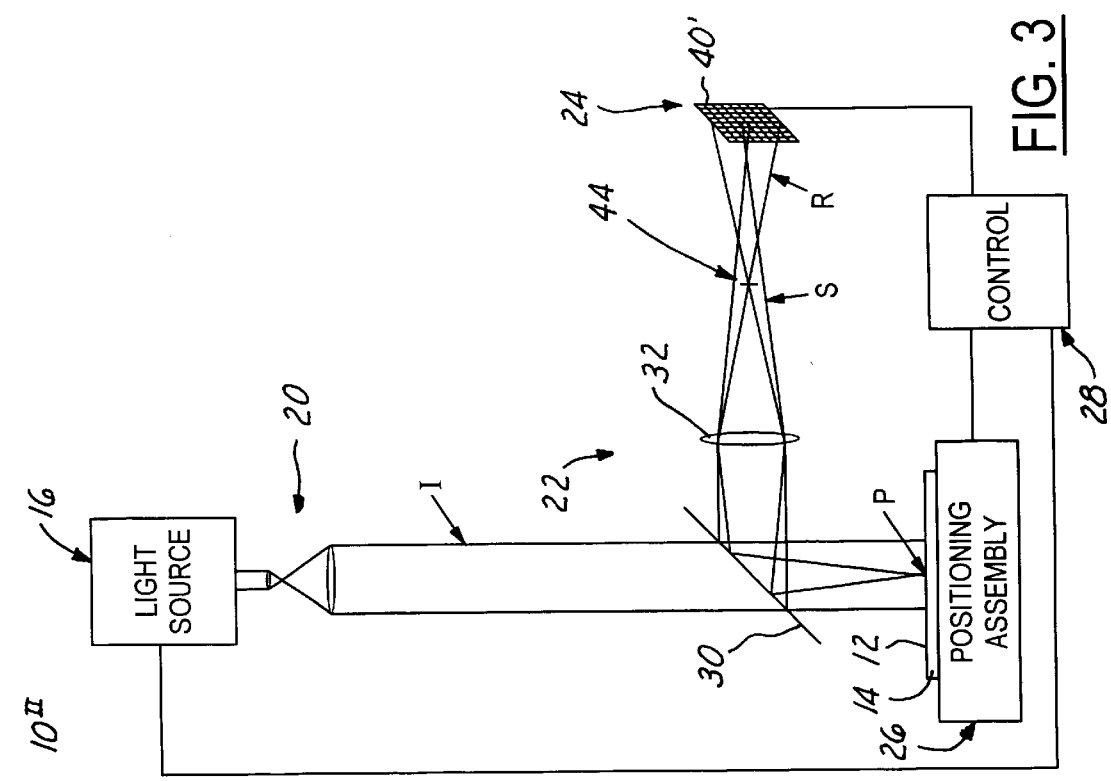
FIG. 3 is a diagrammatic representation of the embodiment of FIG. 2 illustrating an alternate structure to attenuate a bias term, according to the present invention.

FIG. 3 shows another embodiment of the present invention, namely, apparatus $10^{II}$. The method of attenuating the reference beam is the only difference between the embodiments of FIG. 2 and FIG. 3. In the latter case, a narrow band-pass spatial filter 44 is placed at the focal point 35 of the lens system 32. This spatial filter (e.g., pinhole) is used to control the intensity and cone angle of the reference beam R. Signal processing is the same as described above in connection with apparatus 10.

FIG. 4 illustrates yet another embodiment of the present invention, namely, apparatus $10^{III}$. Apparatus $10^{III}$ is a multi-channel device using an optical system only slightly modified from that shown in FIG. 2. The modification comprises the addition of a cylindrical lens 46 after lens system 32 to focus wafer surface 12 on the CCD 40' in one dimension while leaving an orthogonal dimension still slightly defocused. By optically compressing in one dimension, the subsequent digital processing by controller 28 is reduced to being done in only the other, single orthogonal dimension. This configuration provides the capability of having numerous independent detection channels on a CCD area array (i.e., each "row" or "column"—depending on which dimension is compressed—may be considered as a completely independent entity).

The focused dimension can be either parallel to the direction of travel of the wafer or perpendicular to it. The camera has two-dimensional CCD area array 40' operating in a TDI mode. The CCD registers are clocked so that the electronic charge packets are transferred at the same rate and in the same direction as the image. The image signal can be integrated for a much longer time than is allowed by the temporary storage time of a single pixel with a corresponding increase in sensitivity. Data is again being simultaneously collected and transferred out as the wafer scan is in progress. It has the further advantage of averaging out any non-uniformities in each column and gives an enhanced signal to noise ratio.

The result of the configuration of apparatus $10^{III}$ is the establishment of a multi-channel detection device. The subsequent digital processing need only compress the signal in one dimension with the resultant simplification. In particular, the data processing is, in one embodiment, as follows. For apparatus $10^{III}$ (and $10^{IV}$ shown in FIG. 5), the holographic data is one-dimensional (a function of either x or y only). In other words, the holographic data from a particle P is recorded in one line of the CCD output. The two dimensional processing described above is reduced to a one-dimensional processing algorithm. One line by one line, the data can then be processed in the manner similar to that described above.

Figure 5:
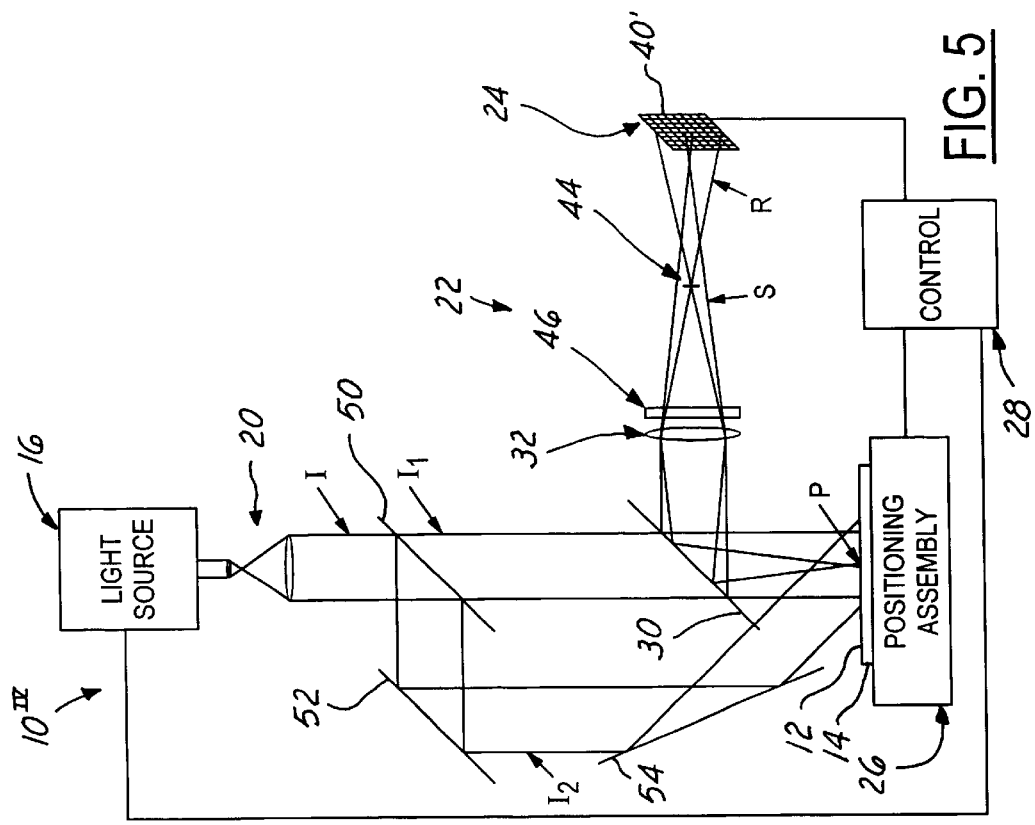
FIG. 5 is a diagrammatic representation of the embodiment of FIG. 4 using a dual illumination path according to the present invention.

FIG. 5 shows yet another embodiment of the present invention namely apparatus $10^{IV}$. With this configuration, a "modified" Mach-Zehnder type of optical arrangement is used. A top view of apparatus $10^{IV}$ is nearly identical to that shown in the previous figures. A side-view apparatus $10^{IV}$, such as shown in FIG. 5, reveals that an additional optical path has been added. After collimation, light beam I from source 16 is incident on a beam-splitter 50. The beam $I_1$ continues and passes through the beam-splitter 30 and is used as described previously. The separated illumination beam $I_2$ is used to illuminate the wafer surface by means of a pair of mirrors 52 and 54. The beam $I_2$ strikes wafer surface 12 at a slight angle to normal incidence. The presence of a particle P, or particles, gives rise to a cone of backscattered radiation S. The two beams R and S are re-combined at beam-splitter 30 and incident on the CCD 40' after passing through the lens systems 32 and 46. As before, lens system 32 is a spherical lens which presents a slightly out-of-focus image of the wafer surface to the CCD 40'. The lens system 46 is a cylindrical lens which is used to focus the wafer surface on the CCD chip in one dimension while leaving an orthogonal dimension still slightly defocused. The focused dimension can be either parallel to the direction of travel of the wafer or perpendicular to it. Modification of the relative beam intensities can now be done directly by inserting appropriate filters in the paths of the separated beams. The result of this arrangement is the establishment of a dual-illumination-beam, multi-channel detection device.

As in FIG. 4, above, the CCD of the camera is used in a TDI mode and the subsequent digital processing need only compress the signal in one dimension to detect the interference pattern.

The present invention also includes a method for identifying the composition of a detected particle P. This can be done by replacing the photodetector 24 (whether a single or array configuration) with a spectroscopic detector 56 (FIG. 6), and the laser (single wavelength) with a white light source or a laser with multiple lines. Note that the composition identification can be done after the particle detection described above has been completed. Composition analysis need therefore be done only at wafer locations where a particle P was previously detected. This means that the entire surface need not be scanned for composition analysis.

Figure 6:
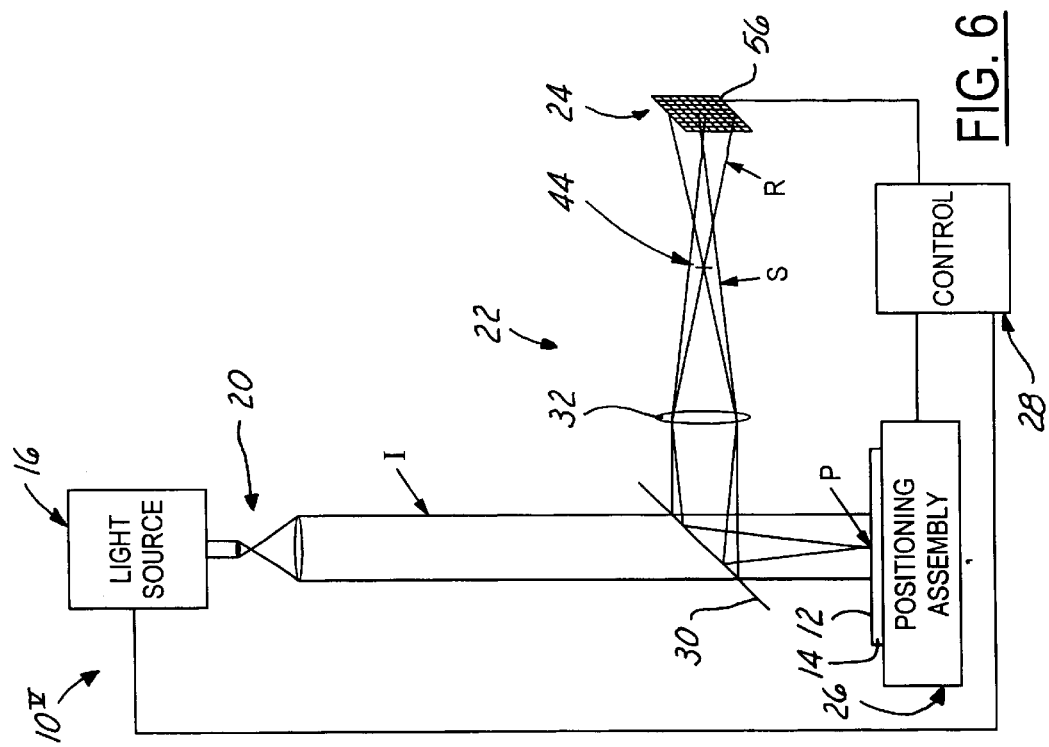
FIG. 6 is a diagrammatic representation of a holographic scatterometer embodiment configured for particle composition analysis according to the present invention.

FIG. 6 illustrates apparatus $10^V$ including composition analysis capability. Apparatus $10^V$ is almost identical to apparatus $10^I$ (FIG. 2), and therefore the description of the configuration shown in FIG. 2 is applicable to the configuration of FIG. 6, except that the source 16 and detector 24 have been replaced (as described above) with spectroscopic detector 56. For example, in one embodiment, using the multi-line laser, individual wavelengths can be selected (and their complex refraction observed), or, a grating could be employed so the wavelength selection could be made at the CCD camera location. The previously referred to CCDs 40 and 40' may still be used. The output of the system (after filtering) is a spectroscopic output $2|a||b(\lambda, t)|$ for every wavelength which the light source contains. Note that this "spectrum" is only dependent on the complex refractive index of the material. It is not dependent on scattering angle, since the particle size is small with respect to wavelength and this results in only Rayleigh scattering. If adequate background information on the possible contaminant materials (i.e., collected ahead of time and stored for subsequent use to thereby define predetermined data), is available, controller 28 can identify the particle composition, providing that the signal is detected from a single particle. This assumption is valid for most wafer surface inspection cases where, at most, only a few such small particles are expected on the surface of the wafer. For example, the characteristic response of a variety of contaminants of interest may be empirically determined during a "calibration" phase of any particular embodiment (i.e., introduce a known contaminant, characterize the response, and record the same).

The previously described embodiments use a dispersed interference signal which is sampled by the pixels of a CCD camera. FIGS. 1–3 and FIG. 6 require a two-dimensional digital compression algorithm. The systems described in FIGS. 4 and 5 optically compress the signal (containing the interference pattern) in one dimension and use digital processing to compress the signal in the orthogonal direction. In each of these cases, several samples of the previously described interference pattern are recorded. The minimum number of samples required to uniquely detect a particle P on a wafer surface 12 is, however, only two. If the two samples are orthogonal components of the field (i.e., separated by Π/2 wavelengths), they can be used to represent the field at that point as a complex number with the two samples being the magnitude of the real and imaginary parts of such a number. The magnitude of this complex number is then the magnitude of the backscattered radiation from a particle P on the wafer surface 12. The absolute phase of the samples need not be known to retrieve the magnitude of the detected signal.

Figure 7:
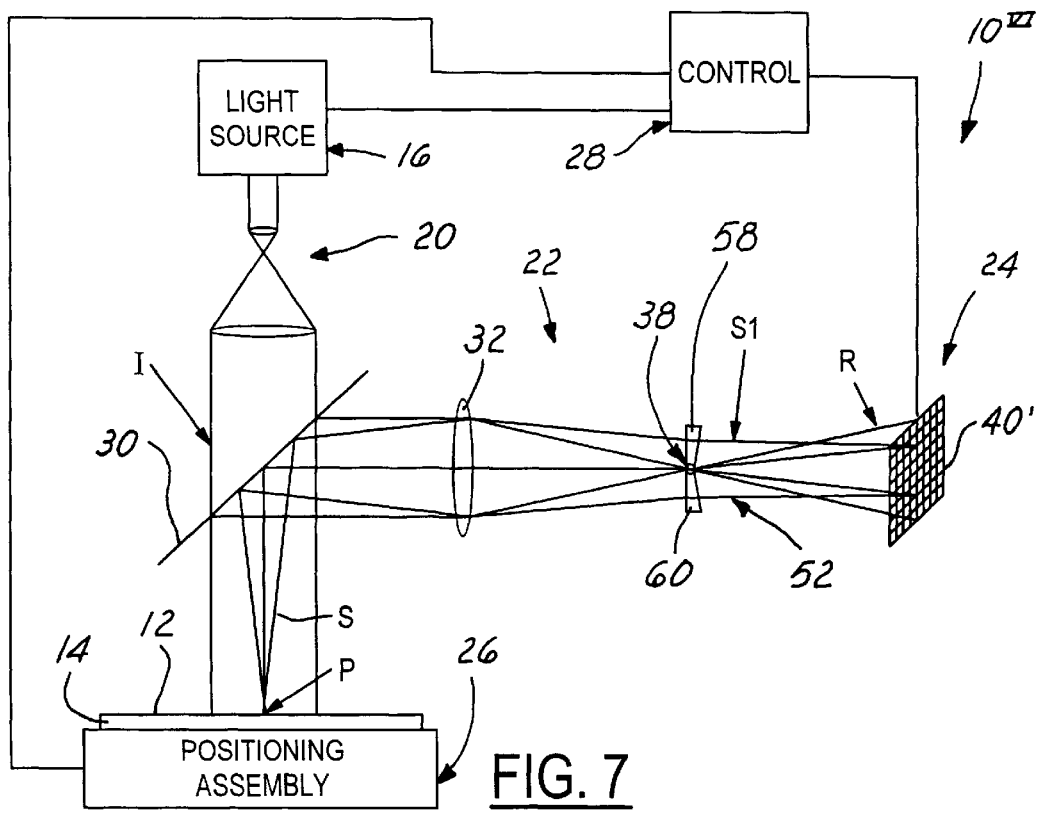
FIG. 7 is a diagrammatic representation of a still yet another holographic scatterometer embodiment according to the present invention.

FIG. 7 illustrates yet another embodiment, namely apparatus $10^{VI}$, of a holographic scatterometer which requires only two samples. FIG. 7 illustrates an optical configuration with the illumination beam I normal to the wafer surface 12. The light source 16, optics 20, and beam-splitter 30 have functions similar to those components described previously. The reference beam R is the specular reflection from wafer surface 12. The wafer surface 12 is focused on a CCD 40' by the optical assembly 22. In a focal plane of the imaging optical system comprising lens 32, a pair of optical wedges 58 and 60 have been inserted. The wedges 58 and 60 cause a phase shift and deviate the signal beam passing through each to a different, unique (respectively) section of CCD array 40'. The wedges 58 and 60 are designed and/or adjusted so the phase shift between the two beams differs by Π/2 wavelengths. The reference beam (R), after attenuation by the neutral density filter 38, recombines with the signal beams, forming paired interference patterns on the CCD surface (i.e., detector plane). The photo-electron signals from corresponding pixels (i.e., pixels which contain an image from the same point on the wafer surface), are now used as the components of a complex number. If a particle P is present, the magnitude of this complex number is directly proportional to the magnitude of the backscattered signal. These signals can be recorded by the CCD camera with a single exposure. If a frame transfer CCD camera is used, the data can be read out and processed off-line without interruption of the data collection process.

Figure 8:
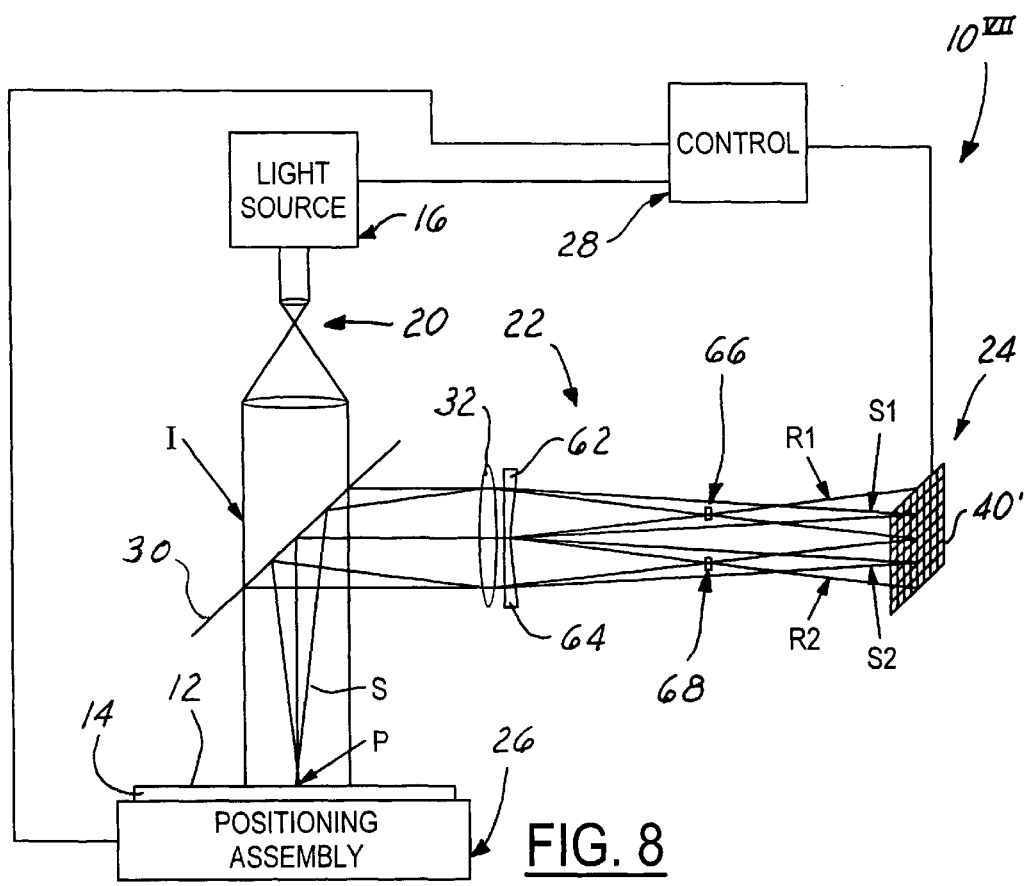
FIG. 8 is a diagrammatic representation of an alternative embodiment to that shown in FIG. 7, according to the present invention.

In this embodiment, data processing may be conducted as follows. Remember, the two points have a 90 degree phase difference with respect to the reference wave. The processed image is generally given as:

$$Ipro(m,n)=[(I(m,n)-<I(m,n)>)^2+(I(m-\Delta m,n+\Delta n)-<I(m,n)>)^2]^{1/2} \quad (7)$$

where $\Delta m$ and $\Delta n$ are the spacing between the two focused points (in terms of pixel element) shown in either FIG. 7 or FIG. 8. Since the two points can be focused on one line of the CCD, the nth line of the processed image becomes:

$$Ipro(m)=[(I(m)-<I(m)>)^2+(I(m-\Delta m)-<I(m)>)^2]^{1/2} \quad (8)$$

FIG. 8 illustrates yet another embodiment, namely apparatus $10^{VII}$. The components for apparatus $10^{VII}$ are as described in FIG. 7 for apparatus $10^{VI}$, but the optical wedges 58 and 60 have been replaced by optical wedges 62 and 64, which have the identical shape and are placed directly behind the optics 32. Since wedges 62 and 64 are identical, an identical phase shift is introduced into each of the two deflected beams. The reference beam R also passes through wedges 62 and 64 and is split into two components. Two neutral density filters, 66 and 68, are used to both attenuate the reference beams and to introduce an appropriate phase shift in each. If the phase shift is Π/2 wavelengths, the desired paired interference patterns will again be present on the CCD detector plane. The photo-electron signals from corresponding pixels (i.e., pixels which contain an image from the same point on the wafer surface), are again used as the components of a complex number. If a particle is present, the magnitude of this complex number is directly proportional to the magnitude of the backscattered signal. These signals can be recorded by the CCD 40' with a single exposure. If a frame transfer CCD camera is used, the data can be read out and processed off-line without interruption of the data collection process. Data processing is as described above.

When a four point focus image system (i.e., FIG. 8) (where each point has a 90 degree phase difference with respect to the reference wave) is used, the processing to obtain the final image can be expressed as:

$$I_{pro}(m)=[(I(m)-I(m-2\Delta m))^2+(I(m-\Delta m)-I(m-3\Delta m))^2]^{1/2} \quad (9)$$

where the four images are focused on one line and the spacing between the focused images is $\Delta m$.

EXAMPLE

Let A equal the intensity of a single pixel corresponding to a phase difference between the signal beam S and the reference beam R, namely, $\theta$; B equal to the intensity of another pixel (in the same line) corresponding to $\theta+90°$; C equal to the intensity of yet another pixel (in the same line) corresponding to $\theta+180°$; and D equal to the intensity of still another pixel (in the same line) corresponding to $\theta+270°$. Evaluating equation (9) yields:

$$I_{pro}(m)=[(A-C)^2-(B-D)^2]^{1/2}$$

In the TDI mode of operation, a "constellation" of 4 points gets brighter and brighter when a particle P is present on surface 12. Two phases may also be used rather than four.

Figure 9:
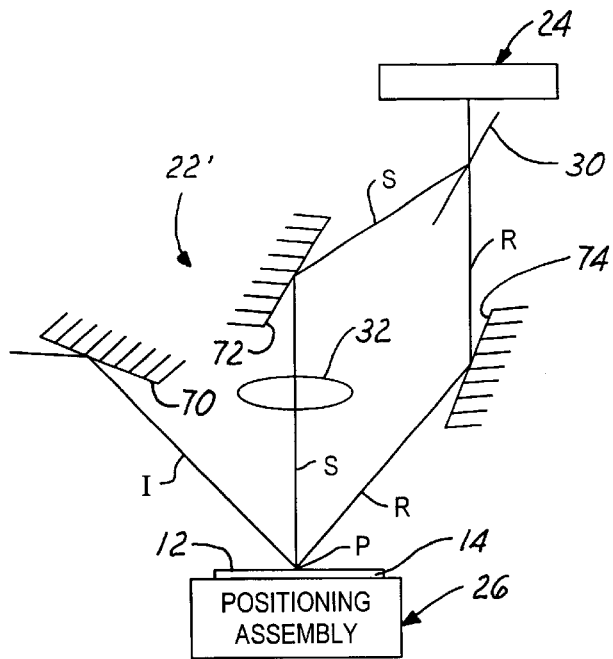
FIG. 9 is a diagrammatic representation of a preferred, alternate arrangement of the optical assembly shown in FIGS. 1A, and 2–8.

FIG. 9 shows an alternate, preferred, arrangement for the optical assembly 22 illustrated in FIGS. 1A, and 2–8. In particular, assembly 22' still includes beam splitter 30 and lens 32, but in addition further includes reflecting surfaces 70, 72, and 74. The advantage provided by assembly 22' is that the reference beam R does not pass through lens 32. Accordingly, the configuration tends to minimize or reduce undesirable air/glass reflections that arise when beam R enters and exits lens 32 (as in the configurations illustrated in FIGS. 1A, and 2–8). The illumination beam I may still preferably impinge surface 12 at near normal incidence. Assembly 22' may be substituted for assembly 22 in the embodiments illustrated in FIGS. 1A, and 2–8. Components, such as 38, 44, 46, 58, 60, 62, 64, 66, and 68 may be disposed intermediate beam splitter 30 and photodetector 24.

Figure 10:
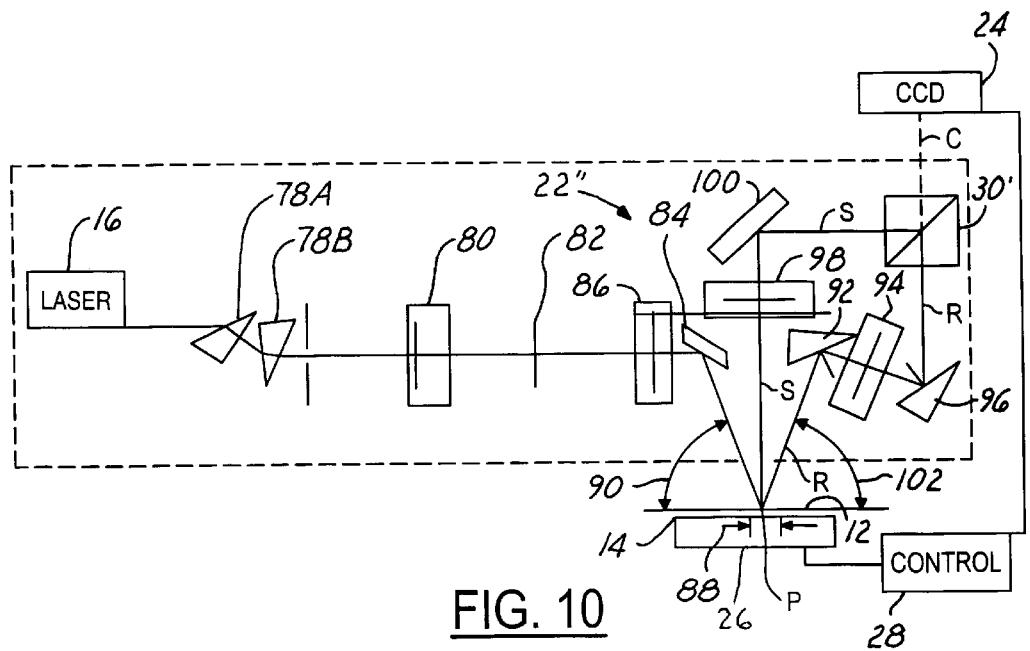
FIG. 10 is a diagrammatic representation of another arrangement of the optical assembly.

FIG. 10 shows an alternate arrangement for the optical assembly 22 illustrated in FIGS. 1A, and 2–8. In particular, assembly 22" includes prisms 78A and 78B positioned to receive light from laser light source 16. Prisms 78A and 78B are preferably two identical prisms mounted at an incident angle to the illumination beam. The prism pair produces an expansion of the beam in one direction only, an amorphic expansion, while shifting the beam a small amount laterally. A magnifying telescope 80 directs the beam through a filter 82 such as a slit and is directed to mirror 84 through a lens 86. Mirror 84 directs the beam to illuminate a field of view 88 on wafer surface 12 of wafer 14. A positioning assembly 16 such as that shown is used to move and position wafer 14. As illustrated, angle 90 is about 70 degrees. This corresponds to 20 degrees from the vertical line. The reference beam R is directed to CCD 24 through a prism or mirror 92, a lens 94, another mirror or lens 96, and combining beam splitter 30'. The scattered beam from particle P is directed vertically through spherical and cylindrical lens 98 and is reflected by a mirror or prism 100 to beam splitter 30'. The scattered beam S is directed to the photo detector surface 24 so that the focus point is before the surface of CCD 24 in a manner such as that described in the previous embodiments. Beam splitter 30' combines the reference beam R and the scattered beam from particle P at beam splitter into a combination beam C which is directed at CCD surface 24. The combined beam forms an interference pattern or image. The interference pattern image is preferably focused before the surface of the detector.

Reference beam R is preferably reflected from wafer surface 12 at an angle 102. Preferably, the illumination angle 90 and angle 102 are the same. Although 70 degrees is mentioned for angle 90, various angles may be used. Preferably, angles 90 and 102 are between about 60 degrees and about 80 degrees.

In this embodiment, a Millenia II laser which has high power but short coherent length was used. In FIG. 10, it is useful to have both optical paths closely matched in length. By slight rotations of the prisms lenses 78A and 78B, the optical paths may be slightly changed to exactly match.

Preferably, the photo detector 24 is a CCD camera that is operated continuously in the TDI mode. That is, the controller 28 moves wafer 14 at the same speed as the image within the CCD photo detector is moved. That is, the CCD has charge packets formed due to the image which are moved simultaneously with the wafer 14. As the time increases the charge on the charge packet corresponding to an image also increases. Any contaminant particle in the optical system will not move with the wafer and CCD and therefore the charge associated with an extraneous particle not on the wafer surface will have a very low relative charge. Thus, the signal to noise ratio of the interference pattern of a particle on the surface of the wafer is substantially greater than any contaminants in the system.

The data from photo detector 24 is simultaneously and continuously collected as the wafer scan is in progress. This allows integrating the light as a function of time to allow the signal to be accumulated to a detectable level without the need for an intense, tightly focused illumination beam with its attendant risk of possible wafer surface damage. Another advantage is the discrimination against any airborne particles although moving, will be at a different rate and a different direction than the wafer scan direction. This is of particular important to minimize the effects of Rayleigh scattering from the ambient. Also, the integration process will average the overall system noise, which is static, and does not move with the charge packets. It should also be noted in FIG. 10 that single lines representing the center of the beam are used for the reference beam and scattered beam. However, as mentioned above, the illumination beam actually illuminates an area on the wafer surface rather than a particular point. This allows a more rapid surface scan from previously known systems.

An apparatus for inspecting a surface of an object, such as a semiconductor wafer, has the following advantages. First, since particles in the air do not move in sychronism with the wafer surface/CCD image movement, they "smear" out— thus, the apparatus is operable in air, able to discriminate between wafer surface deposits and particles in the air (or in any place other than the wafer surface). Second, the inventive apparatus detects such particles through the establishment of an interference pattern, which permits resolution of contaminant particles in the 20 nm to 100 nm range, and microroughness in the 0.1 to 1 nm range. Third, the apparatus achieves particle detection by non-destructive (and non-contact) techniques. Fourth, "volume density" and the composition of the foreign particles may be determined by the apparatus. The composition analysis information may then be applied in statistical process control (SPC) of the fabrication process. Fifth, the apparatus is configured for relatively rapid scans, permitting its use "in-line" (e.g., 300 mm wafer in less than one minute). Sixth, embodiments of the invention are configured for long working distances (e.g., greater than 10 mm). Finally, embodiments of the invention are suitable for use with gallium arsenide, silicon, and other single crystal films grown by molecular beam epitaxy or chemical vapor deposition.

Although the present invention has been described in an illustrative manner, it should be understood that the terminology used is intended to be in the nature of words of description, rather than of limitation.

Thus, the preceding description is exemplary rather than limiting in nature. The preferred embodiments of this invention have been disclosed to enable one skilled in the art to practice this invention. Variations and modifications are possible without departing from the purview and spirit of this invention; the scope of which is limited only by the appended claims.

What is claimed is:

1. An apparatus for inspecting a surface of an object comprising:
   a light source configured to generate an illumination light beam, said illumination beam when incident upon a particle on the surface being scattered to define a scattered beam;
   a photodetector;
   an optical assembly configured to direct said scattered beam and a reference beam derived from said illumination beam to said photodetector;
   a positioning assembly configured to provide a movement of said object such that said surface moves relative to said illumination beam;
   a controller coupled to said photodetector configured to detect the presence of said particle in accordance with a spatial interference pattern from a superposition of said reference beam and said scattered beam.

2. The apparatus of claim 1 wherein said positioning assembly includes means responsive to a drive control signal for controlling said movement to a substantially constant velocity.

3. The apparatus of claim 2 wherein said positioning assembly includes a linear slide positioner.

4. The apparatus of claim 1 wherein said optical assembly comprises:
   a beam-splitter optically intermediate said light source and said surface, and
   wherein said beam-splitter is configured such that said illumination beam strikes the surface at substantially normal incidence.

5. The apparatus of claim 1 wherein said light source comprises:
   a device configured to emit a coherent light signal.

6. The apparatus of claim 5 wherein said reference beam comprises a specular reflection of said illumination beam by the surface.

7. The apparatus of claim 6 wherein said photodetector comprises a charge-coupled device (CCD) forming charge packets corresponding to said interference pattern.

8. The apparatus of claim 7 wherein said charge packets move synchronously with said movement of said positioning assembly.

9. The apparatus of claim 7 wherein said photodetector has a detector plane associated therewith, and,
   wherein said optical assembly comprises a converging lens assembly having an optical axis associated therewith, said lens assembly being configured to produce a focused image in an image plane located at a predefined location along said optical axis, and,
   wherein said detector plane is offset along said optical axis from said image plane by a predefined defocus distance.

10. The apparatus of claim 9 wherein said optical assembly further includes a neutral density filter optically intermediate said converging lens assembly and said photodetector.

11. The apparatus of claim 9 wherein said charge-coupled device (CCD) comprises a plurality of picture elements arranged as a two-dimensional imaging area array, and wherein said controller is configured to operate said CCD in a Time Delay Integration (TDI) mode.

12. The apparatus of claim 11 wherein said optical assembly includes a spatial filter.

13. The apparatus of claim 12 wherein said optical assembly further includes a cylindrical lens assembly configured to compress said interference pattern in at least one dimension.

14. The apparatus of claim 13 wherein said illumination beam is a first illumination beam and said optical assembly further comprises:
   (i) a beam-splitter configured to generate a second illumination beam;
   (ii) a first mirror; and,
   (iii) a second mirror wherein said first and second mirrors are configured to direct said second illumination beam toward the surface at an oblique angle of incidence.

15. The apparatus of claim 7 further including a spectrometer configured to determine one or more characteristics of said particle.

16. The apparatus of claim 7 wherein said CCD comprises a plurality of picture elements arranged as a two-dimensional imaging area array, and said controller is configured to operate said CCD in a Time Delay and Integration (TDI) mode, and wherein said optical assembly includes:
   (i) a converging lens assembly having an optical axis associated therewith;
   (ii) a first optical device disposed along said optical axis and configured to introduce a first phase shift; and
   (iii) a second optical device disposed along said optical axis and configured to introduce a second phase shift different from said first phase shift by Π/2 wavelengths.

17. The apparatus of claim 16 wherein said first and second optical devices comprise optical wedges and are operative to form first and second interference patterns.

18. The apparatus of claim 7 wherein said CCD comprises a plurality of picture elements arranged as a two-dimensional imaging array, and said controller is configured to operate said CCD in a Time Delay and Integration (TDI) mode synchronously with said movement.

19. The apparatus of claim 7 wherein said optical assembly includes:
   (i) a converging lens assembly having an optical axis associated therewith;
   (ii) first and second optical devices disposed along said optical axis and configured to introduce a first phase shift; and,
   (iii) first and second neutral density filters disposed along said optical axis and configured to introduce a phase shift of approximately Π/2 wavelengths.

20. The apparatus of claim 19 wherein said first and second optical devices comprise optical wedges, and wherein said optical assembly is operative to form first, second, third and fourth interference patterns on said CCD.

21. The apparatus of claim 20 wherein said optical assembly is operative to form said first, second, third, and fourth interference patterns as points at respective distinct locations on said CCD array.

22. The apparatus of claim 1 wherein said optical assembly includes
   (i) a beam splitter,
   (ii) a plurality of mirrors to direct said illumination beam to said surface and to redirect a specular reflection thereof defining said reference beam to said beam splitter, and (iii) a lens assembly configured to direct said scattered beam to said beam splitter.

23. A method of inspecting a wafer surface comprising the steps of:
(A) directing an illumination beam to the wafer surface;
(B) moving the wafer surface relative to the illumination beam;
(C) generating a reference beam when the illumination beam impinges on the surface;
(D) generating a scattered beam when the illumination light beam impinges on a particle on the wafer surface;
(E) detecting the presence of the particle in accordance with an interference pattern formed by a superposition of the reference beam and the scattered beam by moving an image of the scattered beam within a detection device synchronously with the step of moving the wafer.

24. The method of claim 23 wherein step (E) comprises the steps of:
splitting the interference pattern into a plurality of components; and,
detecting an amplitude difference as a function of the plurality of interference components.

25. The method of claim 23 further comprising the step of applying matched filter to said interference pattern to obtain a location and magnitude of said particle.

26. An apparatus for inspecting a surface of an object comprising:
a light source configured to generate an illumination light beam over a field of view area of the surface, said illumination beam when incident upon a particle on the surface being scattered to define a scattered beam;
a photodetector having a plurality of elements;
an optical assembly configured to direct said scattered beam and a reference beam derived from said illumination beam to said photodetector, said optical assembly providing a defocused beam to said photodetector;
a positioning assembly configured to move said object such that said surface moves relative to said illumination beam;
a controller coupled to said photodetector and said positioning assembly configured to detect the presence of said particle in accordance with a spatial interference pattern from a superposition of said reference beam and said scattered beam.

27. A method of inspecting a wafer surface comprising the steps of:
directing an illumination beam to the wafer surface;
generating a reference beam when the illumination beam impinges on the surface;
generating a scattered beam when the illumination light beam impinges on a particle on the wafer surface;
defocusing the scatted beam at the surface of a detector;
forming an interference pattern image formed by a superposition of the reference beam and the scattered beam within the detector;
synchronously moving the wafer surface relative to the illumination beam and the image within the detector; and
detecting the presence of the particle in accordance with the interference pattern image.

28. A method as recited in claim 27 wherein the step of detecting comprises determining a location and magnitude of said particle.

29. A method as recited in claim 27 wherein the step of directing an illumination beam comprises directing the illumination beam at a predetermined angle less than ninety degrees.

* * * * *